US011236341B2

(12) United States Patent
Rossi et al.

(10) Patent No.: US 11,236,341 B2
(45) Date of Patent: Feb. 1, 2022

(54) RNA APTAMERS AGAINST TRANSFERRIN RECEPTOR (TFR)

(71) Applicants: City of Hope, Duarte, CA (US); Apterna Ltd, London (GB)

(72) Inventors: John J. Rossi, Azusa, CA (US); Sorah Yoon, Pasadena, CA (US); Nagy Habib, London (GB)

(73) Assignees: City of Hope, Duarte, CA (US); Apterna Ltd, London (GB)

( * ) Notice: Subject to any disclaimer, the term of this patent is extended or adjusted under 35 U.S.C. 154(b) by 774 days.

(21) Appl. No.: 15/519,074

(22) PCT Filed: Oct. 15, 2015

(86) PCT No.: PCT/US2015/055792
§ 371 (c)(1),
(2) Date: Apr. 13, 2017

(87) PCT Pub. No.: WO2016/061386
PCT Pub. Date: Apr. 21, 2016

(65) Prior Publication Data
US 2017/0226515 A1    Aug. 10, 2017

Related U.S. Application Data

(60) Provisional application No. 62/064,310, filed on Oct. 15, 2014.

(51) Int. Cl.
| | |
|---|---|
| *C12N 15/115* | (2010.01) |
| *A61K 31/7105* | (2006.01) |
| *A61K 51/00* | (2006.01) |
| *A61P 35/00* | (2006.01) |
| *G01N 33/574* | (2006.01) |
| *C07K 14/705* | (2006.01) |
| *A61K 47/54* | (2017.01) |
| *A61K 31/713* | (2006.01) |
| *A61K 45/06* | (2006.01) |
| *G01N 33/53* | (2006.01) |

(52) U.S. Cl.
CPC .......... *C12N 15/115* (2013.01); *A61K 31/713* (2013.01); *A61K 31/7105* (2013.01); *A61K 45/06* (2013.01); *A61K 47/549* (2017.08); *C07K 14/70582* (2013.01); *G01N 33/5308* (2013.01); *G01N 33/57492* (2013.01); *C12N 2310/16* (2013.01); *C12N 2310/351* (2013.01); *C12N 2310/3519* (2013.01); *C12N 2320/31* (2013.01); *G01N 2333/70582* (2013.01)

(58) Field of Classification Search
None
See application file for complete search history.

(56) References Cited

U.S. PATENT DOCUMENTS

| | | |
|---|---|---|
| 5,849,890 A | 12/1998 | Gold et al. |
| 2003/0180744 A1 | 9/2003 | Gold et al. |
| 2004/0137010 A1 | 7/2004 | Wilson et al. |
| 2017/0226515 A1 | 8/2017 | Rossi et al. |

FOREIGN PATENT DOCUMENTS

| | | |
|---|---|---|
| WO | WO-2004/026260 A2 | 4/2004 |
| WO | WO-2004/026260 A3 | 4/2004 |
| WO | WO-2013/163303 A2 | 10/2013 |
| WO | WO-2013/163303 A3 | 10/2013 |
| WO | WO-2016/127216 A1 | 8/2016 |

OTHER PUBLICATIONS

Hasegawa et al, Methods for Improving Aptamer Binding Affinity, Molecules 2016, 2, pp. 1-15.*
Imashimizu et al, Single-round isolation of diverse RNA aptamers from a random sequence pool, Biology Methods and Protocols, 2018, 1-13.*
Bennett, K.L. et al. (May 15, 2007). "Tumor suppressor activity of CCAAT/enhancer binding protein alpha is epigenetically down-regulated in head and neck squamous cell carcinoma," *Cancer Res* 67(10):4657-4664.
Chen, C.H. et al. (Oct. 14, 2008, e-published Oct. 6, 2008). "Aptamer-based endocytosis of a lysosomal enzyme," *PNAS USA* 105(41):15908-15913.
Dang, W. et al. (Jun. 2014). "The controversial world of sirtuins," *Drug Discov Today Technol* 12:e9-e17.
Herskovits, A.Z. et al. (Jun. 2013, e-published May 21, 2013). "Sirtuin deacetylases in neurodegenerative diseases of aging," *Cell Res* 23(6):746-758.
Hu, J. et al. (2014). "Inhibition of monocyte adhesion to brain-derived endothelial cells by dual functional RNA chimeras," *Mol Ther Nucleic Acids* 3:e209.
International Search Report dated Mar. 11, 2016, for PCT Application No. PCT/US2015/055792, filed Oct. 15, 2015, 5 pages.
Jin, S. et al. (Jan.-Feb. 2007, e-published Jan. 3, 2007). "Role of autophagy in cancer: management of metabolic stress," *Autophagy* 3(1):28-31.
MacDonald, J. et al. (Apr. 19, 2017, e-published Jan. 25, 2017). "Development of a Bifunctional Aptamer Targeting the Transferrin Receptor and Epithelial Cell Adhesion Molecule (EpCAM) for the Treatment of Brain Cancer Metastases," *ACS Chem Neurosci* 8(4):777-784.

(Continued)

*Primary Examiner* — Maria Marvich
(74) *Attorney, Agent, or Firm* — Mintz Levin Cohn Ferris Glovsky and Popeo, P.C.

(57) ABSTRACT

Provided herein, inter alia, are nucleic acid compounds capable of binding transferrin receptor on a cell and internalizing into said cell. The compositions provided herein may be useful for delivering therapeutic and diagnostic agents to a cell. Further provided are pharmaceutical compositions and methods of treatment using nucleic acid compounds provided herein.

16 Claims, 8 Drawing Sheets

Specification includes a Sequence Listing.

(56) References Cited

OTHER PUBLICATIONS

Maier, K.E. et al. (May 24, 2016). "A New Transferrin Receptor Aptamer Inhibits New World Hemorrhagic Fever Mammarenavirus Entry," *Mol Ther Nucleic Acids* 5:e321.

Meyer, C. et al. (2011, e-published Aug. 28, 2011). "Cell-specific aptamers as emerging therapeutics," *J Nucleic Acids* 2011:904750.

Mu, C. et al. (2013, e-published Mar. 21, 2013). "Solubilization of flurbiprofen into aptamer-modified PEG-PLA micelles for targeted delivery to brain-derived endothelial cells in vitro," *J Microencapsul* 30(7):701-708.

Ni, S. et al. (2017). "Chemical Modifications of Nucleic Acid Aptamers for Therapeutic Purposes," *Int. J. Mol. Sci.* 18:1683.

Porciani, D. et al. (Jan. 28, 2014). "Two interconvertible folds modulate the activity of a DNA aptamer against transferrin receptor," *Mol Ther Nucleic Acids* 3:e144.

Qian, Z.M. et al. (Dec. 2002). "Targeted drug delivery via the transferrin receptor-mediated endocytosis pathway," *Pharmacol Rev* 54(4):561-587.

Tada, Y. et al. (Mar. 15, 2006). Epigenetic Modulation of Tumor Suppressor CCAAT/Enhancer Binding Protein α in Lung Cancer, *Journal of the National Cancer Institute* 98(6):396-406.

Tuerk, C. et al. (1997). "Using the SELEX combinatorial chemistry process to find high affinity nucleic acid ligands to target molecules," *Methods Mol Biol* 67:219-230.

Wilner, S.E. et al. (May 15, 2012). "An RNA alternative to human transferrin: a new tool for targeting human cells," *Mol Ther Nucleic Acids* 1:e21.

Zhou, J. et al. (Feb. 2010). "Aptamer-targeted cell-specific RNA interference," *Silence* 1(1):4.

Zhou, J. et al. (Feb. 2011, e-published Dec. 23, 2010). "Cell-specific aptamer-mediated targeted drug delivery," *Oligonucleotides* 21(1):1-10.

Zhou, J. et al. (Mar. 2017, e-published Nov. 3, 2016). "Aptamers as targeted therapeutics: current potential and challenges," *Nat Rev Drug Discov* 16(3):181-202.

Zuker, M. (Jul. 1, 2003). "Mfold web server for nucleic acid folding and hybridization prediction," *Nucleic Acids Res.* 31(13):3406-3415.

\* cited by examiner

TR14

TR18

SEQUENCE LISTING

```
<160> NUMBER OF SEQ ID NOS: 4

<210> SEQ ID NO 1
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 1
gggagacaag aauaaacgcu caaugcguuc acguuuauuc acauuuuuga auugagcaug        60
agcuucgaca ggaggcucac aacaggc                                           87

<210> SEQ ID NO 2
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 2
gggagacaag aauaaacgcu caaugcguuu acguuuauuc acauuuuuga auugagcaug        60
agcuucgaca ggaggcucac aacaggc                                           87

<210> SEQ ID NO 3
<211> LENGTH: 43
<212> TYPE: RNA
<213> ORGANISM: Artificial Sequence
<220> FEATURE:
<223> OTHER INFORMATION: Synthetic polynucleotide

<400> SEQUENCE: 3
ggggcucaau gcguucacgu uuauucacau uuugaauug agc                          43

<210> SEQ ID NO 4
<211> LENGTH: 87
```

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (24)..(63)
<223> OTHER INFORMATION: n is any of A, U, G, C

<400> SEQUENCE: 4
gggagacaag aataaacgct caannnnnnn nnnnnnnnnn nnnnnnnnnn nnnnnnnnnn      60
nnnttcgaca ggaggctcac aacaggc                                          87
```

RNA APTAMERS AGAINST TRANSFERRIN RECEPTOR (TFR)

CROSS-REFERENCES TO RELATED APPLICATIONS

This application is a national stage entry under 35 U.S.C. 371 of international application no. PCT/US2015/055792, filed Oct. 15, 2015, which claims the benefit of U.S. Provisional Application No. 62/064,310, filed Oct. 15, 2014, the content of which is incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048440-551N01US_2_ST25.TXT, created Nov. 14, 2019, 1,404 bytes, machine format IBM-PC, MS-Windows operating system, is hereby incorporated by reference.

BACKGROUND OF THE INVENTION

The transferrin receptor (TfR) is a membrane glycoprotein expressed on the cellular surface and mediates cellular uptake of iron from the plasma glycoprotein transferrin. Iron uptake from transferrin involves the binding of transferrin to TfR. The bound transferrin is then internalized through receptor-mediated endocytosis in an endocytic vesicle. The release of transferrin from TfR is induced by a decrease in the pH within the endocytic vescile. TfR is expressed on a broad variety of cells at varying levels. For example, TfR is highly expressed on immature erythroid cells, placental tissue, and rapidly dividing cells, both normal and malignant. Thus, compounds capable of binding to TfR on the surface of TfR-expressing cells and internalizing into the cell would be very useful for targeted delivery of such compounds. Provided herein are compositions and methods addressing these and other needs in the art.

BRIEF SUMMARY OF THE INVENTION

Provided herein, inter alia, are novel nucleic acid compositions capable of binding to a transferrin receptor on a cell and internalizing into the cell. The nucleic acid compositions provided herein are, for example, useful for the delivery of therapeutic and imaging agents into cells expressing a transferrin receptor.

In one aspect, a ribonucleic acid compound capable of binding to a transferrin receptor on a cell and internalizing into the cell is provided.

In one aspect, a ribonucleic acid compound including an RNA sequence having at least 80% sequence identity to SEQ ID NO:1, SEQ ID NO:2 or SEQ ID NO:3 is provided and the RNA sequence is at least 50 nucleotides in length.

In one aspect, a ribonucleic acid compound including an RNA sequence having at least 80% sequence identity to SEQ ID NO:1, SEQ ID NO:2 or SEQ ID NO:3 is provided and the RNA sequence is at least 40 nucleotides in length.

In another aspect, a pharmaceutical formulation including the ribonucleic acid compound provided herein including embodiments thereof and a pharmaceutically acceptable excipient is provided.

In another aspect, a pharmaceutical formulation including the ribonucleic acid compound provided herein including embodiments thereof and a therapeutic agent is provided.

In another aspect, a method of delivering a compound moiety into a cell is provided. The method includes (i) contacting a cell with the ribonucleic acid provided herein including embodiments thereof, and (ii) allowing the ribonucleic acid compound to bind to a transferrin receptor on the cell and pass into the cell thereby delivering the compound moiety into the cell.

In another aspect, a method of delivering a compound into a cell is provided. The method includes (i) contacting a cell with a compound and the ribonucleic acid compound provided herein including embodiments thereof, and (ii) allowing the ribonucleic acid compound to bind to a transferrin receptor on the cell and the compound to pass into the cell thereby delivering the compound into the cell.

In another aspect, a method of treating cancer is provided. The method includes administering to a subject in need thereof an effective amount of the ribonucleic acid compound provided herein including embodiments thereof, wherein the ribonucleic acid compound further includes an anticancer therapeutic moiety.

In another aspect, a method of treating cancer is provided. The method includes administering to a subject in need thereof an effective amount of an anticancer agent and the ribonucleic acid compound provided herein including embodiments thereof.

In another aspect, a method of detecting a cell is provided. The method includes (i) contacting a cell with the ribonucleic acid compound provided herein including embodiments thereof, wherein the ribonucleic acid compound further includes an imaging moiety. (ii) The ribonucleic acid compound is allowed to bind to a transferrin receptor on the cell and pass into the cell, and (iii) the imaging moiety is detected thereby detecting the cell.

In another aspect, a method of detecting a cell is provided. The method includes (i) contacting a cell with an imaging agent and the ribonucleic acid compound provided herein including embodiments thereof (ii) The ribonucleic acid compound is allowed to bind to a transferrin receptor on the cell and the imaging agent is allowed to pass into the cell, and (iii) the imaging agent is detected thereby detecting the cell.

DETAILED DESCRIPTION OF THE INVENTION

Definitions

Figure 1:
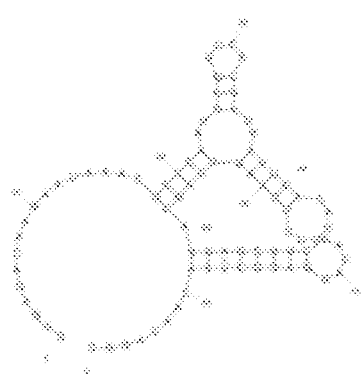
FIG. 1: Mfold structure of aptamer TR14 (SEQ ID NO:1) (left panel) and aptamer TR18 (SEQ ID NO:2) (right panel).
Figure 1:
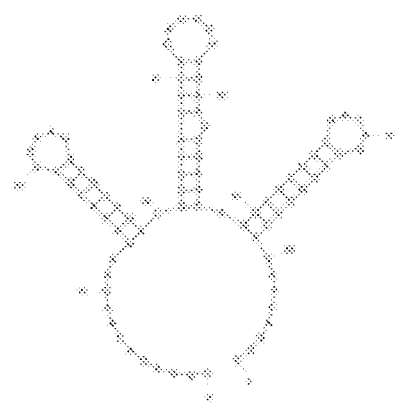

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

The term "aptamer" as provided herein refers to oligonucleotides (e.g. short oligonucleotides or deoxyribonucleotides), that bind (e.g. with high affinity and specificity) to proteins, peptides, and small molecules. Aptamers may have secondary or tertiary structure and, thus, may be able to fold into diverse and intricate molecular structures. Aptamers can be selected in vitro from very large libraries of randomized sequences by the process of systemic evolution of ligands by exponential enrichment (SELEX as described in Ellington AD, Szostak JW (1990) In vitro selection of RNA molecules that bind specific ligands. Nature 346:818-822; Tuerk C, Gold L (1990) Systematic evolution of ligands by exponential enrichment: RNA ligands to bacteriophage T4 DNA polymerase. Science 249:505-510) or by developing SOMAmers (slow off-rate modified aptamers) (Gold L et al. (2010) Aptamer-based multiplexed proteomic technology for biomarker discovery. PLoS ONE 5(12):e15004). Applying the SELEX and the SOMAmer technology includes for instance adding functional groups that mimic amino acid side chains to expand the aptamer's chemical diversity. As a result high affinity aptamers for almost any protein target are enriched and identified. Aptamers exhibit many desirable properties for targeted drug delivery, such as ease of selection and synthesis, high binding affinity and specificity, low immunogenicity, and versatile synthetic accessibility. To date, a variety of anti-cancer agents (e.g. chemotherapy drugs, toxins, and siRNAs) have been successfully delivered to cancer cells in vitro using apatmers.

An "antisense nucleic acid" as referred to herein is a nucleic acid (e.g. DNA or RNA molecule) that is complementary to at least a portion of a specific target nucleic acid (e.g. an mRNA translatable into a protein) and is capable of reducing transcription of the target nucleic acid (e.g. mRNA from DNA) or reducing the translation of the target nucleic acid (e.g. mRNA) or altering transcript splicing (e.g. single stranded morpholino oligo). See, e.g., Weintraub, *Scientific American*, 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid (e.g. target mRNA). In embodiments, the antisense nucleic acid hybridizes to the target nucleic acid sequence (e.g. mRNA) under stringent hybridization conditions. In embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbone modified nucleotides.

In the cell, the antisense nucleic acids hybridize to the corresponding mRNA, forming a double-stranded molecule. The antisense nucleic acids interfere with the translation of the mRNA, since the cell will not translate an mRNA that is double-stranded. The use of antisense methods to inhibit the in vitro translation of genes is well known in the art (Marcus-Sakura, *Anal. Biochem.*, 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or precursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

A "siRNA," "small interfering RNA," "small RNA," or "RNAi" as provided herein, refers to a nucleic acid that forms a double stranded RNA, which double stranded RNA has the ability to reduce or inhibit expression of a gene or target gene when expressed in the same cell as the gene or target gene. The complementary portions of the nucleic acid that hybridize to form the double stranded molecule typically have substantial or complete identity. In one embodiment, a siRNA or RNAi is a nucleic acid that has substantial or complete identity to a target gene and forms a double stranded siRNA. In embodiments, the siRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded siRNA is 15-50 nucleotides in length, and the double stranded siRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

A "saRNA," or "small activating RNA" as provided herein refers to a nucleic acid that forms a double stranded RNA, which double stranded RNA has the ability to increase or activate expression of a gene or target gene when expressed in the same cell as the gene or target gene. The complementary portions of the nucleic acid that hybridize to form the double stranded molecule typically have substantial or complete identity. In one embodiment, a saRNA is a nucleic acid that has substantial or complete identity to a target gene and forms a double stranded saRNA. Typically, the nucleic acid is at least about 15-50 nucleotides in length (e.g., each complementary sequence of the double stranded saRNA is 15-50 nucleotides in length, and the double stranded saRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells, are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

As used herein, the term "conjugate" refers to the association between atoms or molecules. The association can be direct or indirect. For example, a conjugate between a nucleic acid (e.g., ribonucleic acid) and a compound moiety as provided herein can be direct, e.g., by covalent bond, or indirect, e.g., by non-covalent bond. Optionally, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. Thus, the nucleic acids can be attached to a compound moiety through its backbone. Optionally, the ribonucleic acid includes one or more reactive moieties, e.g., an amino acid reactive moiety, that facilitates the interaction of the ribonucleic acid with the compound moiety.

Useful reactive moieties or functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

The reactive functional groups can be chosen such that they do not participate in, or interfere with, the chemical stability of the proteins described herein. By way of example, the nucleic acids can include a vinyl sulfone or other reactive moiety. Optionally, the nucleic acids can include a reactive moiety having the formula S—S—R. R can be, for example, a protecting group. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively.

For specific proteins described herein (e.g., TfR), the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "TfR" as provided herein includes any of the transferrin receptor (TfR) protein naturally occurring forms, homologs or variants that maintain the activity of TfR (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the TfR protein is the protein as identified by the NCBI sequence reference GI:189458817. In embodiments, the TfR protein is the protein as identified by the NCBI sequence reference GI:189458816. In embodiments, the TfR protein is the protein as identified by the NCBI sequence reference GI:189458818. In embodiments, the TfR protein is the protein as identified by the NCBI sequence reference GI:189458817, homolog or functional fragment thereof. In embodiments, the TfR protein is the protein as identified by the NCBI sequence reference GI:189458816, homolog or functional fragment thereof. In embodiments, the TfR protein is the protein as identified by the NCBI sequence reference GI:189458818, homolog or functional fragment thereof. In embodiments, the TfR protein is encoded by a nucleic acid sequence corresponding to Gene ID: 7037.

The term "C/EBPa" or "C/EBPalpha" as provided herein includes any of the CCAAT (cytosine-cytosine-adenosine-adensoine-thyrnidine)/enhancer-binding protein alpha (C/EBPa) naturally occurring forms, homologs or variants that maintain the transcription factor activity of C/EBPalpha (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the C/EBPalpha protein is the protein as identified by the NCBI sequence reference GI:551894998. In embodiments, the C/EBPalpha protein is the protein as identified by the NCBI sequence reference GI:551894998, homolog or functional fragment thereof. In embodiments, the C/EBPalpha protein is encoded by a nucleic acid sequence corresponding to Gene ID: GI:551894997.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), or adrenocortical suppressant (e.g., mitotane, aminoglutethimide), epipodophyllotoxins (e.g., etoposide).

Further examples of anti-cancer agents include, but are not limited to, antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists;

interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein kinase C inhibitors, protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxy-progesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the ribonucleic acid compound described herein can be co-administered with or covalently attached to conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, anti-PD-1 and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the ribonucleic acid compounds described herein can be coadministered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

The term "sample" includes sections of tissues such as biopsy and autopsy samples, and frozen sections taken for histological purposes. Such samples include blood and blood fractions or products (e.g., bone marrow, serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Disease" or "condition" refer to a state of being or health status of a patient or subject capable of being treated with a compound, pharmaceutical composition, or method provided herein. In embodiments, the disease is cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma), an infectious disease (e.g., HIV infection), an inflammatory disease (e.g., rheumatoid arthritis) or a metabolic disease (e.g., diabetes). In embodiments, the disease is a disease related to (e.g. caused by) an aberrant activity of TfR, TfR phosphorylation, or TfR pathway activity, or pathway activated by TfR. In some embodiments, the disease is cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma).

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) or viral disease (e.g., HIV infection associated disease)) is caused by (in whole or in part), or a symptom of the disease is caused by (in whole or in part) the substance or substance activity or function.

The term "aberrant" as used herein refers to different from normal. When used to described enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. Contacting may include allowing two species to react, interact, or physically touch, wherein the two species may be a nucleic acid compound as described herein and a cell (e.g., cancer cell).

Ribonucleic Acid Compounds

The ribonucleic acid compounds provided herein, including embodiments thereof, are, inter alia, capable of binding a transferrin receptor (TfR) on a cell and internalizing into the cell. TfR is expressed within and present on the surface of a broad variety of different cancer cells (e.g., breast cancer, pancreatic cancer, liver cancer, prostate cancer). Therefore, the ribonucleic acid compounds provided herein, including embodiments thereof, may be used to deliver therapeutic or diagnostic molecules into a TfR-expressing cancer cell. The therapeutic or diagnostic molecule may form part of the ribonucleic acid compound provided herein including embodiments thereof. Where the therapeutic or diagnostic molecule forms part (e.g., through covalent attachment) of the ribonucleic acid compound provided herein, including embodiments thereof, the therapeutic or diagnostic molecule is referred to as a "compound moiety" (e.g., therapeutic moiety, imaging moiety). Alternatively, the therapeutic or diagnostic molecule may not form part of the ribonucleic acid compound provided herein, including embodiments thereof, but may be independently internalized by a TfR-expressing cell upon binding of a ribonucleic acid compound provided herein to TfR on said cell. Where the therapeutic or diagnostic molecule does not form part of the ribonucleic acid compound provided herein, the molecule is referred to as a "compound." The ribonucleic acid compounds provided herein including embodiments thereof provide highly specific and efficient means for targeted cancer drug delivery and molecular imaging.

In one aspect, a ribonucleic acid compound capable of binding to a transferrin receptor (TfR) on a cell and internalizing into the cell is provided.

In one aspect, a ribonucleic acid compound including an RNA sequence having at least 80% sequence identity to SEQ ID NO:1, SEQ ID NO:2 or SEQ ID NO:3 is provided and the RNA sequence is at least 40 nucleotides in length. In another aspect, a ribonucleic acid compound including an RNA sequence having at least 80% sequence identity to SEQ ID NO:1, SEQ ID NO:2 or SEQ ID NO:3 is provided and the RNA sequence is at least 50 nucleotides in length. Where the RNA sequence has at least 80% (80% or more) sequence identity to SEQ ID NO:1, SEQ ID NO:2 or SEQ ID NO:3, the RNA sequence may have 80%, 85%, 90%, 91%, 92%, 93%, 94%, 95%, 96%, 97%, 98%, 99% or 100% sequence identity to SEQ ID NO:1, SEQ ID NO:2 or SEQ ID NO:3. In embodiments, the RNA sequence has at least 80% (80% or more) sequence identity to a nucleic acid that hybridizes to a sequence of SEQ ID NO:1, SEQ ID NO:2 or SEQ ID NO:3. Where the RNA sequence is at least 50 (50 nucleotides or more) nucleotides in length, the RNA sequence is at least 50, 55, 60, 65, 70, 75, 80, 85, 90, 95, 100, 110, 120, 130, 140, 150, 160, 170, 180, 190 or 200 nucleotides in length. In embodiments, the RNA sequence is at least 50 nucleotides in length. Where the RNA sequence is at least 40 (40 nucleotides or more) nucleotides in length, the RNA sequence is at least 40, 41, 42, 43, 44, 45, 45, 47, 48, 49, 50, 55, 60, 65, 70, 75, 80, 85, 90, 95, 100, 110, 120, 130, 140, 150, 160, 170, 180, 190 or 200 nucleotides in length. Thus, in embodiments, the RNA sequence is about 43 nucleotides in length.

In embodiments, the RNA sequence includes the sequence of SEQ ID NO:1, SEQ ID NO:2 or SEQ ID NO:3. In embodiments, the RNA sequence is SEQ ID NO:1, SEQ ID NO:2 or SEQ ID NO:3. In embodiments, the RNA sequence is SEQ ID NO:1. In embodiments, the RNA sequence is SEQ ID NO:2. In embodiments, the RNA sequence is SEQ ID NO:3. In embodiments, the RNA sequence is an aptamer. In embodiments, the RNA sequence is about 40 nucleotides in length. In embodiments, the RNA sequence is about 41 nucleotides in length. In embodiments, the RNA sequence is about 42 nucleotides in length. In embodiments, the RNA sequence is about 43 nucleotides in length. In embodiments, the RNA sequence is about 44 nucleotides in length. In embodiments, the RNA sequence is about 45 nucleotides in length. In embodiments, the RNA sequence is about 46 nucleotides in length. In embodiments, the RNA sequence is about 47 nucleotides in length. In embodiments, the RNA sequence is about 48 nucleotides in length. In embodiments, the RNA sequence is about 49 nucleotides in length. In embodiments, the RNA sequence is about 50 nucleotides in length. In embodiments, the RNA sequence is about 51 nucleotides in length. In embodiments, the RNA sequence is about 52 nucleotides in length. In embodiments, the RNA sequence is about 53 nucleotides in length. In embodiments, the RNA sequence is about 54 nucleotides in length. In embodiments, the RNA sequence is about 55 nucleotides in length. In embodiments, the RNA sequence is about 60 nucleotides in length. In embodiments, the RNA sequence is about 65 nucleotides in length. In embodiments, the RNA sequence is about 70 nucleotides in length. In embodiments, the RNA sequence is about 75 nucleotides in length. In embodiments, the RNA sequence is about 80 nucleotides in length. In embodiments, the RNA sequence is about 85 nucleotides in length. In embodiments, the RNA sequence is about 87 nucleotides in length. In embodiments, the RNA sequence is about 95 nucleotides in length. In embodiments, the RNA sequence is about 100 nucleotides in length. In embodiments, the RNA sequence is about 105 nucleotides in length. In embodiments, the RNA sequence is about 110 nucleotides in length.

In embodiments, the RNA sequence has at least 80% sequence identity to SEQ ID NO:1, SEQ ID NO:2 or SEQ ID NO:3 and is at least 30 nucleotides in length. In embodiments, the RNA sequence has at least 80% sequence identity to SEQ ID NO:1, SEQ ID NO:2 or SEQ ID NO:3 and is at least 35 nucleotides in length. In embodiments, the RNA sequence has at least 80% sequence identity to SEQ ID NO:1, SEQ ID NO:2 or SEQ ID NO:3 and is at least 40 nucleotides in length. In embodiments, the RNA sequence has at least 80% sequence identity to SEQ ID NO:1, SEQ ID NO:2 or SEQ ID NO:3 and is at least 45 nucleotides in length. In embodiments, the RNA sequence has at least 80% sequence identity to SEQ ID NO:1, SEQ ID NO:2 or SEQ ID NO:3 and is at least 50 nucleotides in length. In embodiments, the RNA sequence has at least 80% sequence identity to SEQ ID NO:1, SEQ ID NO:2 or SEQ ID NO:3 and is at least 55 nucleotides in length. In embodiments, the RNA sequence has at least 80% sequence identity to SEQ ID NO:1, SEQ ID NO:2 or SEQ ID NO:3 and is at least 60 nucleotides in length. In embodiments, the RNA sequence has at least 80% sequence identity to SEQ ID NO:1, SEQ ID NO:2 or SEQ ID NO:3 and is at least 65 nucleotides in length. In embodiments, the RNA sequence has at least 80% sequence identity to SEQ ID NO:1, SEQ ID NO:2 or SEQ ID NO:3 and is at least 70 nucleotides in length. In embodiments, the RNA sequence has at least 80% sequence identity to SEQ ID NO:1, SEQ ID NO:2 or SEQ ID NO:3 and is at least 75 nucleotides in length. In embodiments, the RNA sequence has at least 80% sequence identity to SEQ ID NO:1, SEQ ID NO:2 or SEQ ID NO:3 and is at least 80 nucleotides in length. In embodiments, the RNA sequence has at least 80% sequence identity to SEQ ID NO:1, SEQ ID NO:2 or SEQ ID NO:3 and is at least 85 nucleotides in length. In embodiments, the RNA sequence has at least 80% sequence identity to SEQ ID NO:1, SEQ ID NO:2 or SEQ ID NO:3 and is at least 90 nucleotides in length. In embodiments, the RNA sequence has at least 80% sequence identity to SEQ ID NO:1, SEQ ID NO:2 or SEQ ID NO:3 and is at least 95 nucleotides in length. In embodiments, the RNA sequence has at least 80% sequence identity to SEQ ID NO:1, SEQ ID NO:2 or SEQ ID NO:3 and is at least 100 nucleotides in length.

In embodiments, the RNA sequence has at least 85% sequence identity to SEQ ID NO:1, SEQ ID NO:2 or SEQ ID NO:3 and is at least 30 nucleotides in length. In embodiments, the RNA sequence has at least 85% sequence identity to SEQ ID NO:1, SEQ ID NO:2 or SEQ ID NO:3 and is at least 35 nucleotides in length. In embodiments, the RNA sequence has at least 85% sequence identity to SEQ ID NO:1, SEQ ID NO:2 or SEQ ID NO:3 and is at least 40 nucleotides in length. In embodiments, the RNA sequence has at least 80% sequence identity to SEQ ID NO:1, SEQ ID NO:2 or SEQ ID NO:3 and is at least 45 nucleotides in length. In embodiments, the RNA sequence has at least 85% sequence identity to SEQ ID NO:1, SEQ ID NO:2 or SEQ ID NO:3 and is at least 50 nucleotides in length. In embodiments, the RNA sequence has at least 85% sequence identity to SEQ ID NO:1, SEQ ID NO:2 or SEQ ID NO:3 and is at least 55 nucleotides in length. In embodiments, the RNA sequence has at least 85% sequence identity to SEQ ID NO:1, SEQ ID NO:2 or SEQ ID NO:3 and is at least 60 nucleotides in length. In embodiments, the RNA sequence has at least 85% sequence identity to SEQ ID NO:1, SEQ ID NO:2 or SEQ ID NO:3 and is at least 65 nucleotides in length. In embodiments, the RNA sequence has at least 85% sequence identity to SEQ ID NO:1, SEQ ID NO:2 or SEQ ID NO:3 and is at least 70 nucleotides in length. In embodiments, the RNA sequence has at least 85% sequence identity to SEQ ID NO:1, SEQ ID NO:2 or SEQ ID NO:3 and is at least 75 nucleotides in length. In embodiments, the RNA sequence has at least 85% sequence identity to SEQ ID NO:1, SEQ ID NO:2 or SEQ ID NO:3 and is at least 80 nucleotides in length. In embodiments, the RNA sequence has at least 85% sequence identity to SEQ ID NO:1, SEQ ID NO:2 or SEQ ID NO:3 and is at least 85 nucleotides in length. In embodiments, the RNA sequence has at least 85% sequence identity to SEQ ID NO:1, SEQ ID NO:2 or SEQ ID NO:3 and is at least 90 nucleotides in length. In embodiments, the RNA sequence has at least 85% sequence identity to SEQ ID NO:1, SEQ ID NO:2 or SEQ ID NO:3 and is at least 95 nucleotides in length. In embodiments, the RNA sequence has at least 85% sequence identity to SEQ ID NO:1, SEQ ID NO:2 or SEQ ID NO:3 and is at least 100 nucleotides in length.

In embodiments, the RNA sequence has at least 90% sequence identity to SEQ ID NO:1, SEQ ID NO:2 or SEQ ID NO:3 and is at least 30 nucleotides in length. In embodiments, the RNA sequence has at least 90% sequence identity to SEQ ID NO:1, SEQ ID NO:2 or SEQ ID NO:3 and is at least 35 nucleotides in length. In embodiments, the RNA sequence has at least 90% sequence identity to SEQ ID NO:1, SEQ ID NO:2 or SEQ ID NO:3 and is at least 40 nucleotides in length. In embodiments, the RNA sequence has at least 80% sequence identity to SEQ ID NO:1, SEQ ID NO:2 or SEQ ID NO:3 and is at least 45 nucleotides in length. In embodiments, the RNA sequence has at least 90% sequence identity to SEQ ID NO:1, SEQ ID NO:2 or SEQ ID NO:3 and is at least 50 nucleotides in length. In embodiments, the RNA sequence has at least 90% sequence identity to SEQ ID NO:1, SEQ ID NO:2 or SEQ ID NO:3 and is at least 55 nucleotides in length. In embodiments, the RNA sequence has at least 90% sequence identity to SEQ ID NO:1, SEQ ID NO:2 or SEQ ID NO:3 and is at least 60 nucleotides in length. In embodiments, the RNA sequence has at least 90% sequence identity to SEQ ID NO:1, SEQ ID NO:2 or SEQ ID NO:3 and is at least 65 nucleotides in length. In embodiments, the RNA sequence has at least 90% sequence identity to SEQ ID NO:1, SEQ ID NO:2 or SEQ ID NO:3 and is at least 70 nucleotides in length. In embodiments, the RNA sequence has at least 90% sequence identity to SEQ ID NO:1, SEQ ID NO:2 or SEQ ID NO:3 and is at least 75 nucleotides in length. In embodiments, the RNA sequence has at least 90% sequence identity to SEQ ID NO:1, SEQ ID NO:2 or SEQ ID NO:3 and is at least 80 nucleotides in length. In embodiments, the RNA sequence has at least 90% sequence identity to SEQ ID NO:1, SEQ ID NO:2 or SEQ ID NO:3 and is at least 85 nucleotides in length. In embodiments, the RNA sequence has at least 90% sequence identity to SEQ ID NO:1, SEQ ID NO:2 or SEQ ID NO:3 and is at least 90 nucleotides in length. In embodiments, the RNA sequence has at least 90% sequence identity to SEQ ID NO:1, SEQ ID NO:2 or SEQ ID NO:3 and is at least 95 nucleotides in length. In embodiments, the RNA sequence has at least 90% sequence identity to SEQ ID NO:1, SEQ ID NO:2 or SEQ ID NO:3 and is at least 100 nucleotides in length.

In embodiments, the RNA sequence has at least 95% sequence identity to SEQ ID NO:1, SEQ ID NO:2 or SEQ ID NO:3 and is at least 30 nucleotides in length. In embodiments, the RNA sequence has at least 95% sequence identity to SEQ ID NO:1, SEQ ID NO:2 or SEQ ID NO:3 and is at least 35 nucleotides in length. In embodiments, the RNA sequence has at least 95% sequence identity to SEQ ID NO:1, SEQ ID NO:2 or SEQ ID NO:3 and is at least 40 nucleotides in length. In embodiments, the RNA sequence has at least 80% sequence identity to SEQ ID NO:1, SEQ ID NO:2 or SEQ ID NO:3 and is at least 45 nucleotides in length. In embodiments, the RNA sequence has at least 95% sequence identity to SEQ ID NO:1, SEQ ID NO:2 or SEQ ID NO:3 and is at least 50 nucleotides in length. In embodiments, the RNA sequence has at least 95% sequence identity to SEQ ID NO:1, SEQ ID NO:2 or SEQ ID NO:3 and is at least 55 nucleotides in length. In embodiments, the RNA sequence has at least 95% sequence identity to SEQ ID NO:1, SEQ ID NO:2 or SEQ ID NO:3 and is at least 60 nucleotides in length. In embodiments, the RNA sequence has at least 95% sequence identity to SEQ ID NO:1, SEQ ID NO:2 or SEQ ID NO:3 and is at least 65 nucleotides in length. In embodiments, the RNA sequence has at least 95% sequence identity to SEQ ID NO:1, SEQ ID NO:2 or SEQ ID NO:3 and is at least 70 nucleotides in length. In embodiments, the RNA sequence has at least 95% sequence identity to SEQ ID NO:1, SEQ ID NO:2 or SEQ ID NO:3 and is at least 75 nucleotides in length. In embodiments, the RNA sequence has at least 95% sequence identity to SEQ ID NO:1, SEQ ID NO:2 or SEQ ID NO:3 and is at least 80 nucleotides in length. In embodiments, the RNA sequence has at least 95% sequence identity to SEQ ID NO:1, SEQ ID NO:2 or SEQ ID NO:3 and is at least 85 nucleotides in length. In embodiments, the RNA sequence has at least 95% sequence identity to SEQ ID NO:1, SEQ ID NO:2 or SEQ ID NO:3 and is at least 90 nucleotides in length. In embodiments, the RNA sequence has at least 95% sequence identity to SEQ ID NO:1, SEQ ID NO:2 or SEQ ID NO:3 and is at least 95 nucleotides in length. In embodiments, the RNA sequence has at least 95% sequence identity to SEQ ID NO:1, SEQ ID NO:2 or SEQ ID NO:3 and is at least 100 nucleotides in length.

In embodiments, the RNA sequence has at least 98% sequence identity to SEQ ID NO:1, SEQ ID NO:2 or SEQ ID NO:3 and is at least 30 nucleotides in length. In embodiments, the RNA sequence has at least 98% sequence identity to SEQ ID NO:1, SEQ ID NO:2 or SEQ ID NO:3 and is at least 35 nucleotides in length. In embodiments, the RNA sequence has at least 98% sequence identity to SEQ ID NO:1, SEQ ID NO:2 or SEQ ID NO:3 and is at least 40 nucleotides in length. In embodiments, the RNA sequence has at least 80% sequence identity to SEQ ID NO:1, SEQ ID NO:2 or SEQ ID NO:3 and is at least 45 nucleotides in length. In embodiments, the RNA sequence has at least 98% sequence identity to SEQ ID NO:1, SEQ ID NO:2 or SEQ ID NO:3 and is at least 50 nucleotides in length. In embodiments, the RNA sequence has at least 98% sequence identity to SEQ ID NO:1, SEQ ID NO:2 or SEQ ID NO:3 and is at least 55 nucleotides in length. In embodiments, the RNA sequence has at least 98% sequence identity to SEQ ID NO:1, SEQ ID NO:2 or SEQ ID NO:3 and is at least 60 nucleotides in length. In embodiments, the RNA sequence has at least 98% sequence identity to SEQ ID NO:1, SEQ ID NO:2 or SEQ ID NO:3 and is at least 65 nucleotides in length. In embodiments, the RNA sequence has at least 98% sequence identity to SEQ ID NO:1, SEQ ID NO:2 or SEQ ID NO:3 and is at least 70 nucleotides in length. In embodiments, the RNA sequence has at least 98% sequence identity to SEQ ID NO:1, SEQ ID NO:2 or SEQ ID NO:3 and is at least 75 nucleotides in length. In embodiments, the RNA sequence has at least 98% sequence identity to SEQ ID NO:1, SEQ ID NO:2 or SEQ ID NO:3 and is at least 80 nucleotides in length. In embodiments, the RNA sequence has at least 98% sequence identity to SEQ ID NO:1, SEQ ID NO:2 or SEQ ID NO:3 and is at least 85 nucleotides in length. In embodiments, the RNA sequence has at least 98% sequence identity to SEQ ID NO:1, SEQ ID NO:2 or SEQ ID NO:3 and is at least 90 nucleotides in length. In embodiments, the RNA sequence has at least 98% sequence identity to SEQ ID NO:1, SEQ ID NO:2 or SEQ ID NO:3 and is at least 95 nucleotides in length. In embodiments, the RNA sequence has at least 98% sequence identity to SEQ ID NO:1, SEQ ID NO:2 or SEQ ID NO:3 and is at least 100 nucleotides in length.

Upon binding TfR on the surface of a cell, the ribonucleic acid compound provided herein (including embodiments thereof) may be internalized by the cell. The term "internalized," "internalizing," or "internalization" as provided herein refers to a composition (e.g., a compound, a ribonucleic acid compound, a therapeutic agent, an imaging agent) being drawn into the cytoplasm of the cell (e.g. after being engulfed by a cell membrane). In embodiments, the cell is a malignant cell. In embodiments, the cell is a breast cancer cell. In embodiments, the cell is a prostate cancer cell. In embodiments, the cell is a liver cancer cell. In embodiments, the cell is a pancreatic cancer cell. In embodiments, the cell is a non-malignant cell.

The ribonucleic acid compound provided herein (including embodiments thereof) may include a compound moiety. Where the ribonucleic acid compound includes a compound moiety, the compound moiety may be covalently (e.g. directly or through a covalently bonded intermediary) attached to the RNA sequence (see, e.g., useful reactive moieties or functional groups used for conjugate chemistries set forth above). Thus, in embodiments, the ribonucleic acid compound further includes a compound moiety covalently attached to the RNA sequence. In embodiments, the compound moiety and the RNA sequence form a conjugate. In embodiments, the compound moiety is non-covalently (e.g. through ionic bond(s), van der Waal's bond(s)/interactions, hydrogen bond(s), polar bond(s), or combinations or mixtures thereof) attached to the RNA sequence.

In embodiments, the compound moiety is a therapeutic moiety or an imaging moiety covalently attached to the RNA sequence. The term "therapeutic moiety" as provided herein is used in accordance with its plain ordinary meaning and refers to a monovalent compound having a therapeutic benefit (prevention, eradication, amelioration of the underlying disorder being treated) when given to a subject in need thereof. Therapeutic moieties as provided herein may include, without limitation, peptides, proteins, nucleic acids, nucleic acid analogs, small molecules, antibodies, enzymes, prodrugs, cytotoxic agents (e.g. toxins) including, but not limited to ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, Pseudomonas exotoxin (PE) A, PE40, abrin, and glucocorticoid. In embodiments, the therapeutic moiety is an anti-cancer agent or chemotherapeutic agent as described herein. In embodiments, the therapeutic moiety is a nucleic acid moiety, a peptide moiety or a small molecule drug moiety. In embodiments, the therapeutic moiety is a nucleic acid moiety. In embodiments, the therapeutic moiety is a peptide moiety. In embodiments, the therapeutic moiety is a small molecule drug moiety. In embodiments, the therapeutic moiety is a nuclease. In embodiments, the therapeutic moiety is an immunostimulator. In embodiments, the therapeutic moiety is a toxin. In embodiments, the therapeutic moiety is a nuclease. In embodiments, the therapeutic moiety is a zinc finger nuclease. In embodiments, the therapeutic moiety is a transcription activator-like effector nuclease. In embodiments, the therapeutic moiety is Cas9.

In embodiments, the therapeutic moiety is an activating nucleic acid moiety (a monovalent compound including an activating nucleic acid) or an antisense nucleic acid moiety (a monovalent compound including an antisense nucleic acid). An activating nucleic acid refers to a nucleic acid capable of detectably increasing the expression or activity of a given gene or protein. The activating nucleic acid can increase expression or activity 10%, 20%, 30%, 40%, 50%, 60%, 70%, 80%, 90% or more in comparison to a control in the absence of the activating nucleic acid. In certain instances, expression or activity is 1.5-fold, 2-fold, 3-fold, 4-fold, 5-fold, 10-fold or higher than the expression or activity in the absence of the activating nucleic acid.

In embodiments, the therapeutic moiety is an miRNA moiety (a monovalent compound including a miRNA), an mRNA moiety (a monovalent compound including an mRNA), an siRNA moiety (a monovalent compound including an siRNA) or an saRNA moiety (a monovalent compound including an saRNA). In embodiments, the therapeutic moiety is a miRNA moiety. The term "miRNA" is used in accordance with its plain ordinary meaning and refers to a small non-coding RNA molecule capable of post-transcriptionally regulating gene expression. In one embodiment, a miRNA is a nucleic acid that has substantial or complete identity to a target gene. In embodiments, the miRNA inhibits gene expression by interacting with a complementary cellular mRNA thereby interfering with the expression of the complementary mRNA. Typically, the miRNA is at least about 15-50 nucleotides in length (e.g., each complementary sequence of the miRNA is 15-50 nucleotides in length, and the miRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length. In embodiments, the therapeutic moiety is a siRNA moiety or saRNA moiety as described herein. In embodiments, the therapeutic moiety is an anticancer agent moiety. In embodiments, the therapeutic moiety is an mRNA moiety. In embodiments, the therapeutic moiety is a siRNA moiety. In embodiments, the therapeutic moiety is a saRNA moiety. In embodiments, the therapeutic moiety is a cDNA moiety. In embodiments, the therapeutic moiety is a C/EBPalpha saRNA moiety. A "C/EBPalpha saRNA" as provided herein is a saRNA capable of activating the expression of a C/EBPalpha protein.

The compound moiety provided herein may be an imaging moiety. An "imaging moiety" as provided herein is a monovalent compound detectable by spectroscopic, photochemical, biochemical, immunochemical, chemical, or other physical means. In embodiments, the imaging moiety is covalently attached to the RNA sequence. Exemplary imaging moieties are without limitation $^{32}$P, radionuclides, positron-emitting isotopes, fluorescent dyes, fluorophores, antibodies, bioluminescent molecules, chemoluminescent molecules, photoactive molecules, metals, electron-dense reagents, enzymes (e.g., as commonly used in an ELISA), magnetic contrast agents, quantum dots, nanoparticles, biotin, digoxigenin, haptens and proteins or other entities which can be made detectable, e.g., by incorporating a radiolabel into a peptide or antibody specifically reactive with a target peptide. Any method known in the art for conjugating an antibody to the moiety may be employed, e.g., using methods described in Hermanson, *Bioconjugate Techniques* 1996, Academic Press, Inc., San Diego. Exemplary fluorophores include fluorescein, rhodamine, GFP, coumarin, FITC, AlExa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese. In embodiments, the imaging moiety is a bioluminescent molecule. In embodiments, the imaging moiety is a photoactive molecule. In embodiments, the imaging moiety is a metal. In embodiments, the imaging moiety is a nanoparticle.

Pharmaceutical Formulations

Pharmaceutical compositions of the ribonucleic acid compounds provided herein may include compositions having a therapeutic moiety contained in a therapeutically effective amount, i.e., in an amount effective to achieve its intended purpose. The pharmaceutical compositions of the ribonucleic acid compounds provided herein may include compositions having imaging moieties contained in an effective amount, i.e., in an amount effective to achieve its intended purpose. The actual amount effective for a particular application will depend, inter alia, on the condition being treated, tested, detected, or diagnosed. When administered in methods to treat a disease, such compositions will contain an amount of active ingredient effective to achieve the desired result, e.g., modulating the activity of a target molecule, and/or reducing, eliminating, or slowing the progression of disease symptoms. Determination of a therapeutically effective amount of a therapeutic moiety provided herein is well within the capabilities of those skilled in the art, especially in light of the detailed disclosure herein. When administered in methods to diagnose or detect a disease, such compositions will contain an amount of an imaging moiety described herein effective to achieve the desired result, e.g., detecting the absence or presence of a target molecule, cell, or tumor in a subject. Determination of a detectable amount of an imaging moiety provided herein is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compositions described herein including embodiments thereof. Adjustment and manipulation of established dosages (e.g., frequency and duration) are well within the ability of those skilled in the art.

For any composition (e.g., the ribonucleic acid compounds provided, combinations of an anticancer agent and the ribonucleic acid compound provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

In another aspect, a pharmaceutical formulation including the ribonucleic acid compound as provided herein including embodiments thereof and a pharmaceutically acceptable excipient is provided. In embodiments, the ribonucleic acid includes a compound moiety covalently attached to the RNA sequence. As described above, the compound moiety may be a therapeutic moiety or an imaging moiety covalently attached to the RNA sequence.

In another aspect, the pharmaceutical formulation includes the ribonucleic acid compound as provided herein including embodiments thereof and a therapeutic agent. In embodiments, the ribonucleic acid compound and the therapeutic agent are not covalently attached. A therapeutic agent as provided herein refers to a composition (e.g. compound, drug, antagonist, inhibitor, modulator) having a therapeutic effect. In embodiments, the therapeutic agent is an anticancer agent. In embodiments, the pharmaceutical formulation includes a pharmaceutically acceptable excipient.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Methods of Delivery

As described above the ribonucleic acid compounds provided herein including embodiments thereof may be used to deliver compound moieties or compounds (e.g., therapeutic agents or an imaging agents) into a cell. Where a compound moiety (e.g., therapeutic moiety or imaging moiety) is delivered into a cell, the compound moiety may be covalently attached to the ribonucleic acid compound (RNA sequence) provided herein including embodiments thereof. Upon binding of the ribonucleic acid compound (RNA sequence) to TfR on a cell, the compound moiety is internalized by the cell while being covalently attached to the ribonucleic acid compound (RNA sequence). Thus, in one aspect, a method of delivering a compound moiety into a cell is provided. The method includes, (i) contacting a cell with the ribonucleic acid compound as provided herein including embodiments thereof and (ii) allowing the ribonucleic acid compound to bind to a TfR on the cell and pass into the cell thereby delivering the compound moiety into the cell.

Alternatively, where a compound is delivered into a cell, the compound (e.g., a therapeutic agent or an imaging agent) may not be covalently attached to the ribonucleic acid compound (RNA sequence). Upon binding of the nucleic acid compound provided herein including embodiments thereof to TfR on a cell, the nucleic acid compound and the compound provided are internalized by the cell without being covalently attached to each other. Thus, in another aspect, a method of delivering a compound into a cell is provided. The method includes (i) contacting a cell with a compound and the ribonucleic acid compound as provided herein including embodiments thereof and (ii) allowing the ribonucleic acid compound to bind to a TfR on the cell and the compound to pass into the cell thereby delivering the compound into the cell. In embodiments, the compound is a therapeutic agent or imaging agent. In embodiments, the compound is non-covalently attached to the ribonucleic acid compound.

Methods of Treatment

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma). For example certain methods herein treat cancer by decreasing or reducing or preventing the occurrence, growth, metastasis, or progression of cancer; or treat cancer by decreasing a symptom of cancer. Symptoms of cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) would be known or may be determined by a person of ordinary skill in the art.

Where combination treatments are contemplated, it is not intended that the agents (i.e. ribonucleic acid compounds) described herein be limited by the particular nature of the combination. For example, the agents described herein may be administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent.

An "effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"Patient" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In embodiments, a patient is human.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

In another aspect, a method of treating cancer is provided. The method includes administering to a subject in need thereof an effective amount of the ribonucleic acid compound as provided herein (including embodiments thereof) wherein the ribonucleic acid compound further includes an anticancer therapeutic moiety. In another aspect, a method of treating cancer is provided. The method includes administering to a subject in need thereof an effective amount of an anticancer agent and a ribonucleic acid compound as provided herein including embodiments thereof.

Methods of Detecting a Cell

The nucleic acid compositions provided herein may also be used for the delivery of compounds and compound moieties to a cell expressing TfR. As described above, the compounds and compound moieties delivered may be imaging agents useful for cell detections. Thus, in one aspect, a method of detecting a cell is provided. The method includes (i) contacting a cell with the ribonucleic acid compound as provided herein including embodiments thereof, wherein the ribonucleic acid compound further includes an imaging moiety. (ii) The ribonucleic acid compound is allowed to bind to a transferrin receptor on the cell and pass into the cell. (iii) The imaging moiety is detected thereby detecting the cell.

In another aspect, a method of detecting a cell is provided. The method includes (i) contacting a cell with an imaging agent and the ribonucleic acid compound as provided herein including embodiments thereof (ii) The ribonucleic acid compound is allowed to bind to a transferrin receptor on the cell and the imaging agent is allowed to pass into the cell. (iii) The imaging agent is detected thereby detecting the cell.

In embodiments, the cell is a malignant cell. In embodiments, the cell is a breast cancer cell. In embodiments, the cell is a prostate cancer cell. In embodiments, the cell is a liver cancer cell. In embodiments, the cell is a pancreatic cancer cell. In embodiments, the cell is a non-malignant cell. In embodiments, the cell forms part of an organism. In embodiments, the organism is a mammal. In embodiments, the cell forms part of a cell culture.

Examples

Protein SELEX (Systemic Evolution of Ligands by Exponential Enrichment)

The extracellular domain of TfR was purchased from Sino Biological Inc (11020-HO7H). The SELEX cycle was performed basically as described by Tuerk and Gold_ENREF_1 (Tuerk, C., *Methods Mol Biol.*, 67, 219-230 (1997)). In vitro selection was carried out essentially as described as follows. The 2'F-RNA aptamers were selected from randomized sequences. A random library of RNA oligonucleotides of sequence 5'-GGGAGACAAGAATAAACGCTCAA-$N_{40}$-TTCGACAGGAGGCTCACAA CAGGC-3' (SEQ ID NO:4) [N40 represents 40 nucleotide (nt) sequences formed by equimolar incorporation of A, G, C, and U at each position] was constructed by in vitro transcription of synthetic DNA templates with NTPs (2'F UTP, 2'F CTP, GTP, ATP, Epicentre Biotechnologies, Madision, Wis.) and T7 RNA polymerase. To increase the nuclease resistance, 2'F-RNAs were used. To remove RNAs that bind nonspecifically to agarose beads, 1.44 uM of the RNA library was preincubated with 20 ul of Ni-NTA agarose beads in 100 ul binding buffer (30 mM Tris-HCl, 150 mM NaCl, 1.5 mM MgCl2, 2 mM dithiothreitol, and 1% BSA) for 30 min at room temperature with shaking, precipitated by centrifugation, and discarded. The precleared supernatant was transferred to a new tube and incubated with 333 nM of his-tagged TfR for 30 min at room temperature. RNAs which bound to TfR were recovered, amplified by RT-PCR and in vitro transcription, and used in the following selection rounds. In subsequent rounds, capsid concentration was reduced by 2-fold at every 3 round for more stringent condition. After 12 rounds of SELEX, the resulting cDNA was amplified. The amplified DNA was cloned and individual clones were identified by DNA sequencing. Structures of aptamers were predicted using MFOLD (Zuker, M., *Nucleic Acids Res.*, 31, 3406-3415 (2003)), available at http://www.bioinfo.rpi.edu/applications/mfold/using a salt correction algorithm and temperature correction for 25° C.

Biosensor Assays

A BIAcore T100 (GE Healthcare, Uppsala, Sweden) was used to measure binding parameters by surface plasmon resonance (SPR) technique. Briefly, the aptamer templates were amplified and tagged at the 39-end with dT16 by PCR using 5'-template primer and dT16 tagging 3'-template primer. These DNA templates were then transcribed to poly (A)-tailed RNAs. A 5′-biotinylated dT16 oligomer was bound to the surface of the streptavidin sensor chip (GE Healthcare) of flow cells 1 and 2. The poly (A)-tailed RNA was immobilized to about 100 RUs in flow cell 2 by complementary hybridization to the dT16 oligomer. TfR solution of different concentration between 100 and 6 nM was injected to the flow cells 1 and 2 of the sensor chip. Data was obtained by subtracting the flow cell 1 data from the flow cell 2 data, thereby showing the net interaction between RNA and protein. To regenerate the sensor chip, bound material was completely removed by injecting 50mMNaOH. Kinetic constants were estimated by using BIAevaluation 3.0 software (GE Healthcare).

Live Cell Confocal Imaging for Cell Internalization

In order to test the internalization of the selected RNA aptamers in cancer cells, the cells were grown in 35 mm glass bottom dishes (MatTek, Ashland, Mass., USA) with seeding at $1\times10^5$ cells in medium for 24 hrs. The RNAs were labeled with Cy3 using the Cy3 Silencer siRNA labeling kit (Ambion, Tex., USA) following the manufacturer's instructions. Cy3-labeled RNAs at 100 nM were added to the cells and incubated for 1 hour. Following the incubation, the cells were stained with 5 ug/ml Hoechst 33342 (Molecular Probes, Calif., USA) for live cell nuclear staining. The images were taken using a Zeiss LSM 510 Meta Inverted 2 photon confocal microscope system using a C-Apo 40x/1.2NA Water immersion objective.

In Vitro Selection of RNA Aptamers to TfR

A library of 2′F RNAs was used to increase nuclease-resistance and enhance aptamer folding. To isolate 2′F RNA aptamers binding to intact cells, a library of approximately 440 different 2′F RNA molecules, containing a 40-nt-long random sequence flanked by defined sequences, was screened by SELEX. After 12 cycles of selection, the highly enriched aptamer pools were cloned. The sequences of TR14 and TR18 are below and one single nucleotide difference between them. The expected structure by MFold was FIG. 1.

TR14:
(SEQ ID NO: 1)
GGGAGACAAGAAUAAACGCUCAAUGCGUUCACGUUUAUUCACAUUUUGA
AUUGAGCAUGAGCUUCGACAGGAGGCUCACAACAGGC

TR18:
(SEQ ID NO: 2)
GGGAGACAAGAAUAAACGCUCAAUGCGUUUACGUUUAUUCACAUUUUGA
AUUGAGCAUGAGCUUCGACAGGAGGCUCACAACAGGC

TfR RNA Aptamers Specificity and Binding Affinity

Figure 2:
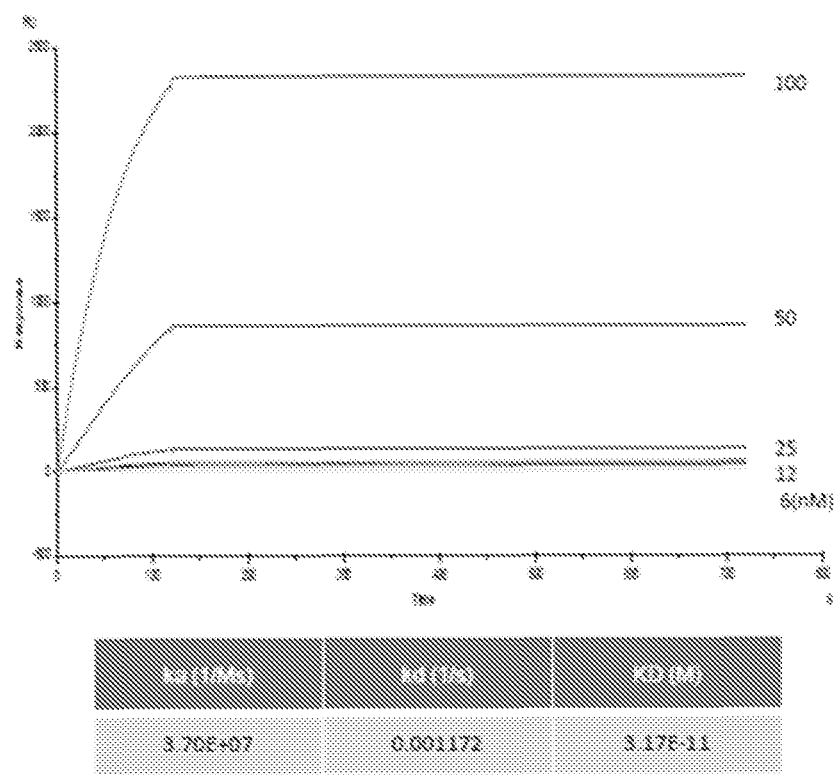
FIG. 2: Kinetics of aptamer TR14.

To confirm the binding and measure the affinity of TR14, SPR was utilized. The measured dissociation constants ($K_D$) was 31.7 pM (FIG. 2).

Cell Internalization in Various Cancer Cells

Figure 3:
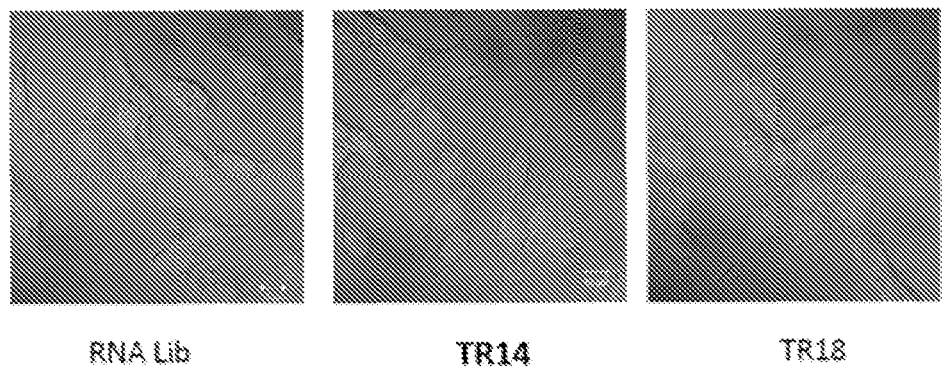
FIG. 3: Cell internalization of a fluorescently (Cy3) labeled control RNA (left panel), Cy3 labeled aptamer TR14 (mid panel) and Cy3 labeled aptamer TR 18 (right panel) in liver cells (HepG2). Nuclear staining was performed using Hoechst.
Figure 4:
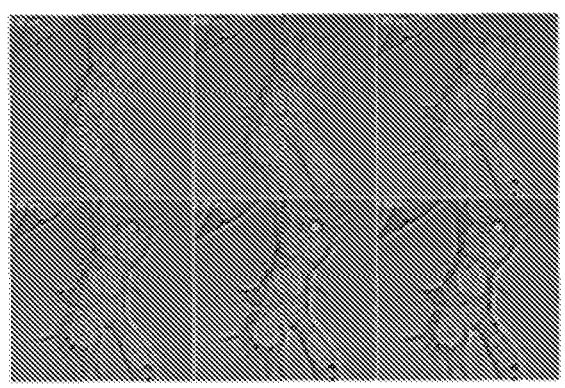
FIG. 4: Cell internalization of fluorescently (Cy3) labeled aptamer TR14 in liver cells (HepG2) (left panel) and pancreatic cells (Mia PaCa-2) (right panel). Nuclear staining was performed using Hoechst.
Figure 4:
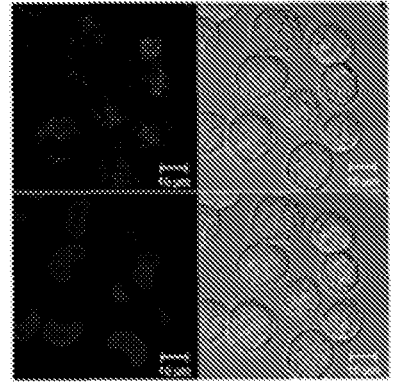
Figure 5:
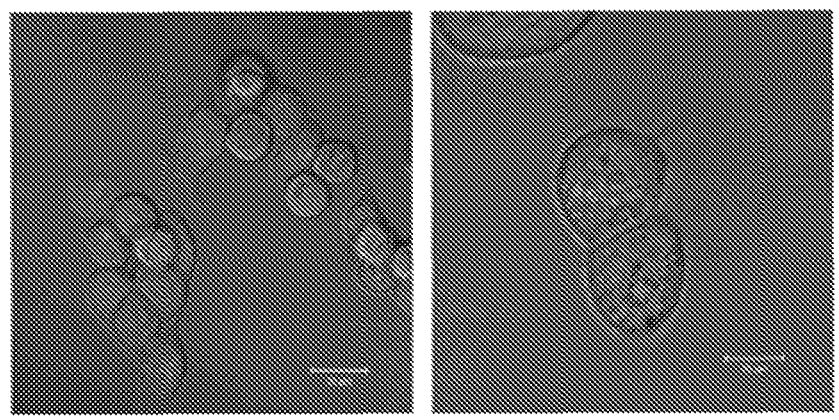
FIG. 5: Cell internalization of fluorescently (Cy3) labeled aptamer TR14 in breast cancer cells (MCF7) (left panel) and prostate cancer cells (PC3) (right panel). Nuclear staining was performed using Hoechst.
Figure 6:
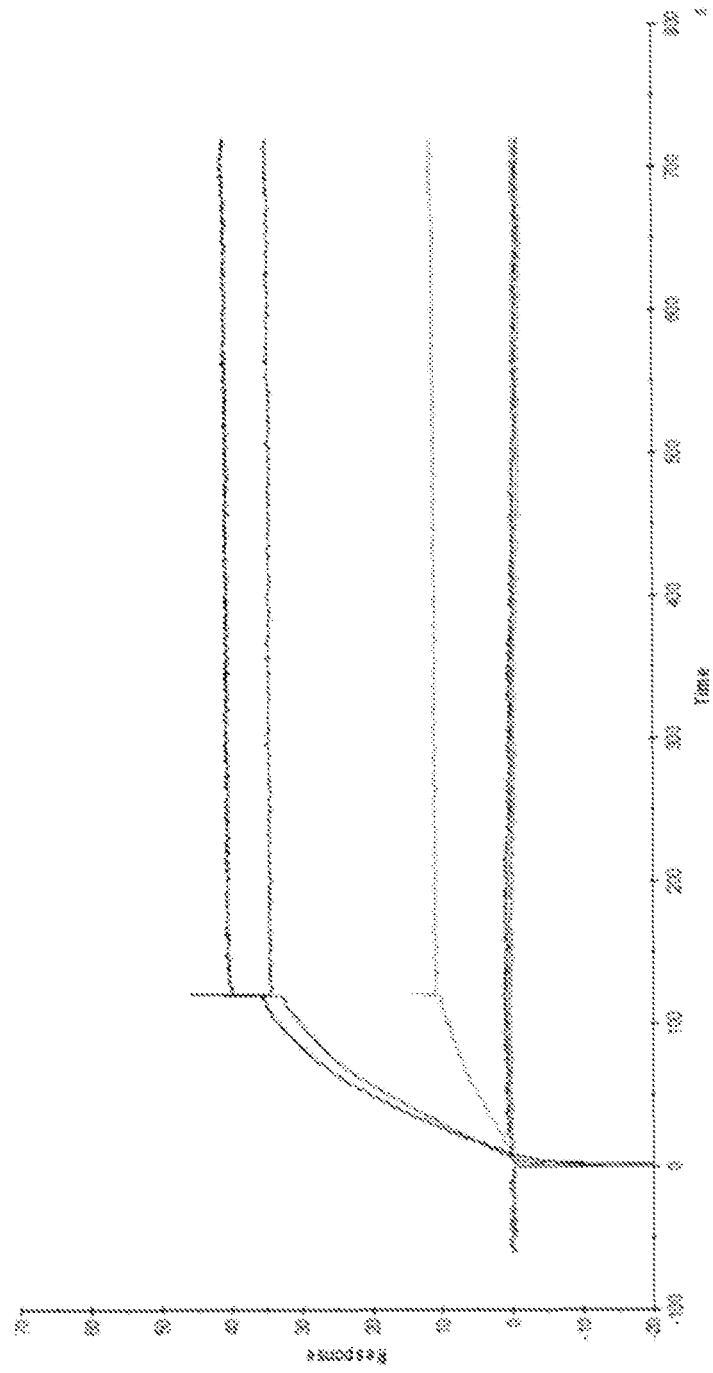
FIG. 6: Kinetics of truncated TfR aptamer (43-mer).
Figure 7:
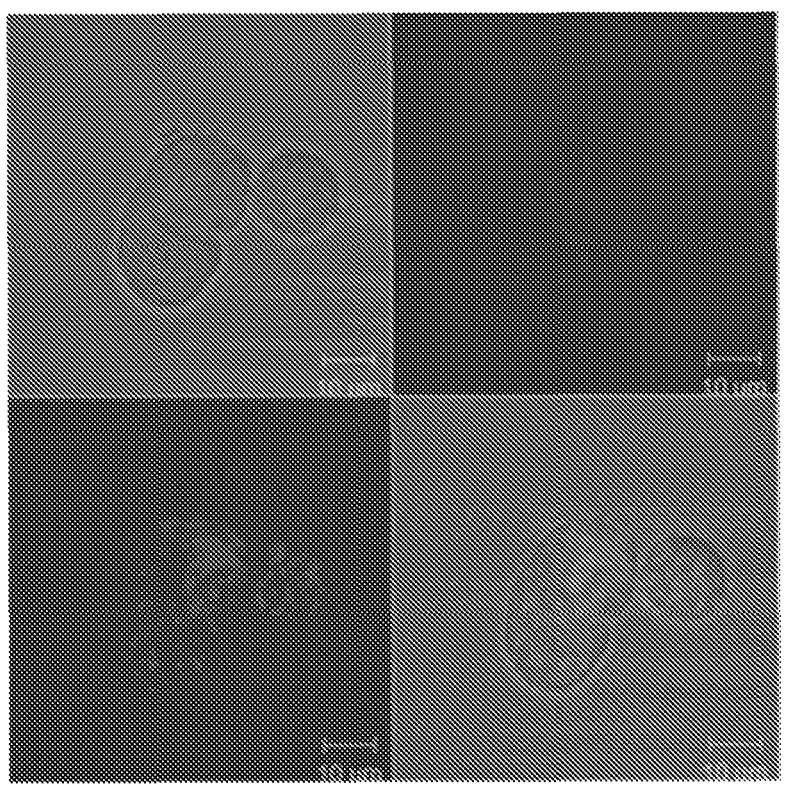
FIG. 7: Cell internalization of a fluorescently labeled truncated TfR aptamer in PANC-1 cells. Top left panel: bright field; top right panel nuclear staining with Hoechst; bottom left panel: localization of Cy5 labeled truncated TfR aptamer; bottom right panel: colocalization of Hoechst and Cy5.
Figure 8:
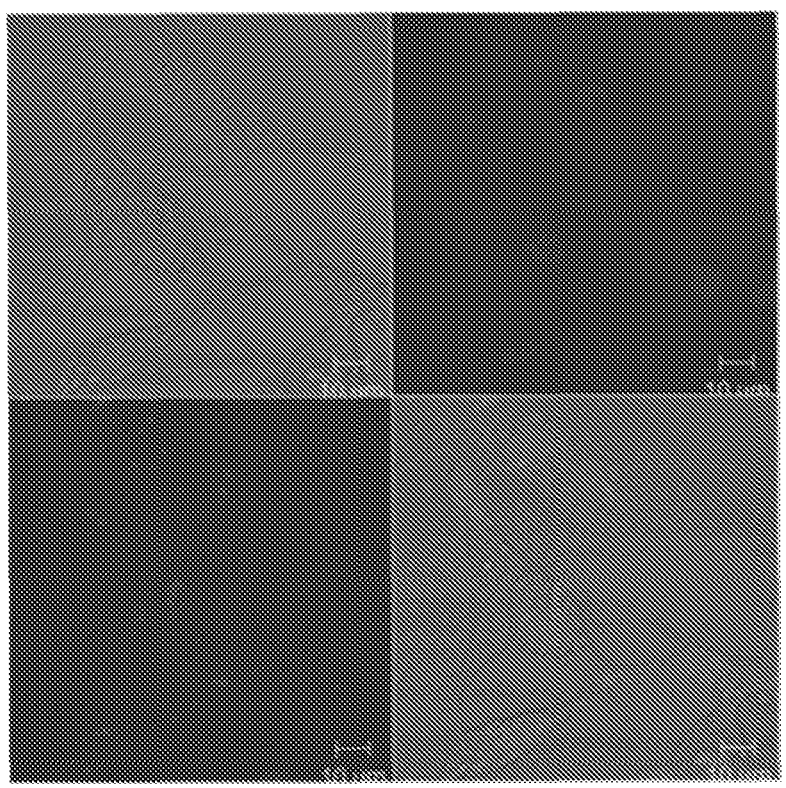
FIG. 8: Cell internalization of a fluorescently labeled truncated TfR aptamer in HegG2 cells. Top left panel: bright field; top right panel nuclear staining with Hoechst; bottom left panel: localization of Cy5 labeled truncated TfR aptamer; bottom right panel: colocalization of Hoechst and Cy5.

To verify the cell internalization for therapeutics delivery, various cancer cells were incubated with fluorescently labeled TR14 RNA (100 nM). As seen in FIG. 3-5, TR14 got internalized in liver, pancreatic, prostate and breast cancer.

TABLE 1

Kinetics of TR14.

| ka (1/Ms) | kd (1/s) | KD (M) |
|---|---|---|
| 3.70E+04 | 0.001172 | 3.17E−11 |

TABLE 2

Kinetics of truncated TfR aptamer:

| ka (1/Ms) | kd (1/s) | KD (M) |
|---|---|---|
| 8.34E+08 | 5.77E−04 | 6.92E−13 |

Informal Sequence Listing

SEQ ID NO: 1 (TR14):
5′ GGGAGACAAGAAUAAACGCUCAAUGCGUUCACGUUUAUUCACAUUUU
UGAAUUGAGCAUGAGCUUCGACAGGAGGCUCACAACAGGC 3′

SEQ ID NO: 2 (TR18):
5′ GGGAGACAAGAAUAAACGCUCAAUGCGUUUACGUUUAUUCACAUUUU
UGAAUUGAGCAUGAGCUUCGACAGGAGGCUCACAACAGGC 3′

SEQ ID NO: 3 (truncated TfR aptamer):
5′ GGGGCUCAAUGCGUUCACGUUUAUUCACAUUUUUGAAUUGAGC 3′

EMBODIMENTS

Embodiment 1. A ribonucleic acid compound comprising an RNA sequence having at least 80% sequence identity to SEQ ID NO:1, SEQ ID NO:2 or SEQ ID NO:3, wherein said RNA sequence is at least 40 nucleotides in length.

Embodiment 2. The ribonucleic acid compound of embodiment 1, wherein said RNA sequence is about 43 nucleotides in length.

Embodiment 3. The ribonucleic acid compound of embodiment 1, wherein said RNA sequence is at least 50 nucleotides in length.

Embodiment 4. The ribonucleic acid compound of one of embodiments 1-3, further comprising a compound moiety covalently attached to said RNA sequence.

Embodiment 5. The ribonucleic acid compound of embodiment 4, wherein said compound moiety is a therapeutic moiety or an imaging moiety covalently attached to said RNA sequence.

Embodiment 6. The ribonucleic acid compound of embodiment 5, wherein said therapeutic moiety is a nucleic acid moiety, a peptide moiety or a small molecule drug moiety.

Embodiment 7. The ribonucleic acid compound of embodiment 5, wherein said therapeutic moiety is an activating nucleic acid moiety or an antisense nucleic acid moiety.

Embodiment 8. The ribonucleic acid compound of embodiment 5, wherein said therapeutic moiety is an miRNA moiety, mRNA moiety, siRNA moiety or saRNA moiety.

Embodiment 9. The ribonucleic acid compound of embodiment 5, wherein said therapeutic moiety is an siRNA moiety or saRNA moiety.

Embodiment 10. The ribonucleic acid compound of one of embodiments 5 to 9, wherein said therapeutic moiety is an anticancer agent moiety.

Embodiment 11. The ribonucleic acid compound of embodiment 5, wherein said therapeutic moiety is a C/EBPalpha saRNA moiety.

Embodiment 12. The ribonucleic acid compound of embodiment 5, wherein said imaging agent moiety is a bioluminescent molecule, a photoactive molecule, a metal or a nanoparticle.

Embodiment 13. The ribonucleic acid compound of one of embodiments 1 or 3 to 12, wherein said RNA sequence is 87 nucleotides in length.

Embodiment 14. The ribonucleic acid compound of one of embodiments 1 to 13, wherein said RNA sequence is SEQ ID NO:1, SEQ ID NO:2 or SEQ ID NO:3.

Embodiment 15. A pharmaceutical formulation comprising the ribonucleic acid compound of one of embodiments 1 to 14 and a pharmaceutically acceptable excipient.

Embodiment 16. A pharmaceutical formulation comprising the ribonucleic acid compound of one of embodiments 1, 2, 13 or 14 and a therapeutic agent.

Embodiment 17. The pharmaceutical formulation of embodiment 16, wherein said therapeutic agent is an anticancer agent.

Embodiment 18. A method of delivering a compound moiety into a cell, the method comprising: (i) contacting a cell with the ribonucleic acid compound of one of embodiments 4 to 14; and (ii) allowing said ribonucleic acid compound to bind to a transferrin receptor on said cell and pass into said cell thereby delivering said compound moiety into said cell.

Embodiment 19. A method of delivering a compound into a cell, the method comprising: (i) contacting a cell with a compound and the ribonucleic acid compound of one of embodiments 1, 2, 13 or 14; and (ii) allowing said ribonucleic acid compound to bind to a transferrin receptor on said cell and said compound to pass into said cell thereby delivering said compound into said cell.

Embodiment 20. The method of embodiment 19, wherein said compound is a therapeutic agent or imaging agent.

Embodiment 21. A method of treating cancer, the method comprising administering to a subject in need thereof an effective amount of the ribonucleic acid compound of one of embodiments 1 to 11, 13 or 14, wherein said ribonucleic acid compound further comprises an anticancer therapeutic moiety.

Embodiment 22. A method of treating cancer, the method comprising administering to a subject in need thereof an effective amount of an anticancer agent and the ribonucleic acid compound of one of embodiments 1, 2, 13 or 14.

Embodiment 23. A method of detecting a cell, the method comprising: (i) contacting a cell with the ribonucleic acid compound of one of embodiments 1 to 5 or 12 to 14, wherein said ribonucleic acid compound further comprises an imaging moiety; (ii) allowing said ribonucleic acid compound to bind to a transferrin receptor on said cell and pass into said cell; and (iii) detecting said imaging moiety thereby detecting said cell.

Embodiment 24. A method of detecting a cell, the method comprising: (i) contacting a cell with an imaging agent and the ribonucleic acid compound of one of embodiments 1, 2, 13 or 14; (ii) allowing said ribonucleic acid compound to bind to a transferrin receptor on said cell and said imaging agent to pass into said cell; and (iii) detecting said imaging agent thereby detecting said cell.

---

What is claimed is:

1. A ribonucleic acid compound comprising an RNA sequence, wherein said RNA sequence is the sequence of SEQ ID NO:1, SEQ ID NO:2 or SEQ ID NO:3.

2. The ribonucleic acid compound of claim 1, further comprising a compound moiety covalently attached to said RNA sequence.

3. The ribonucleic acid compound of claim 2, wherein said compound moiety is a therapeutic moiety or an imaging moiety covalently attached to said RNA sequence.

4. The ribonucleic acid compound of claim 3, wherein said therapeutic moiety is a nucleic acid moiety, a peptide moiety or a small molecule drug moiety.

5. The ribonucleic acid compound of claim 3, wherein said therapeutic moiety is an activating nucleic acid moiety or an antisense nucleic acid moiety.

6. The ribonucleic acid compound of claim 3, wherein said therapeutic moiety is an miRNA moiety, an mRNA moiety, an siRNA moiety or an saRNA moiety.

7. The ribonucleic acid compound of claim 3, wherein said therapeutic moiety is a C/EBPalpha saRNA moiety.

8. A method of delivering a compound moiety into a cell comprising a transferrin receptor, the method comprising:
   (i) directly contacting a cell with the ribonucleic acid compound of claim 4; and
   (ii) allowing said ribonucleic acid compound to bind to a transferrin receptor on said cell and pass into said cell thereby delivering said compound moiety into said cell.

9. A pharmaceutical formulation comprising the ribonucleic acid compound of claim 1 and a pharmaceutically acceptable excipient.

10. A pharmaceutical formulation comprising the ribonucleic acid compound of claim 1 and a therapeutic agent.

11. The pharmaceutical formulation of claim 10, wherein said therapeutic agent is an anticancer agent.

12. A method of delivering a compound into a cell comprising a transferrin receptor, the method comprising:
   (i) directly contacting a cell with a compound and the ribonucleic acid compound of claim 1; and
   (ii) allowing said ribonucleic acid compound to bind to a transferrin receptor on said cell and said compound to pass into said cell thereby delivering said compound into said cell.

13. A method of treating cancer comprising a cell comprising a transferrin receptor, the method comprising intratumorally administering to a subject in need thereof an effective amount of the ribonucleic acid compound of claim 1, wherein said ribonucleic acid compound further comprises an anticancer therapeutic moiety.

14. A method of treating cancer comprising a cell comprising a transferrin receptor, the method comprising intratumorally administering to a subject in need thereof an effective amount of an anticancer agent and the ribonucleic acid compound of claim 1.

15. A method of detecting a cell comprising a transferrin receptor, the method comprising: (i) directly contacting a cell with the ribonucleic acid compound of claim 1, wherein said ribonucleic acid compound further comprises an imaging moiety; (ii) allowing said ribonucleic acid compound to bind to a transferrin receptor on said cell and pass into said cell; and (iii) detecting said imaging moiety thereby detecting said cell.

16. A method of detecting a cell comprising a transferrin receptor, the method comprising: (i) contacting a cell directly with an imaging agent and the ribonucleic acid compound of claim 1; (ii) allowing said ribonucleic acid compound to bind to a transferrin receptor on said cell and said imaging agent to pass into said cell; and (iii) detecting said imaging agent thereby detecting said cell.

* * * * *